(12) United States Patent
Moor et al.

(10) Patent No.: US 8,143,487 B2
(45) Date of Patent: Mar. 27, 2012

(54) RED LETTUCE

(75) Inventors: Cornelis Marinus Moor, Monster (NL);
Egbert Carolus Johannes Smits,
Zevenbergen (NL); Adrianus Martinus Jozeph Ammerlaan, Aramon (FR);
Johannes Wilhelmus Schut, Wouw (NL); Kornelius Reinink, Delft (NL)

(73) Assignee: Rijk Zwaan Zaadteelt En Zaadhandel B.V., De Lier (NL)

( * ) Notice: Subject to any disclaimer, the term of this patent is extended or adjusted under 35 U.S.C. 154(b) by 716 days.

(21) Appl. No.: 12/052,690

(22) Filed: Mar. 20, 2008

(65) Prior Publication Data

US 2009/0106867 A1 Apr. 23, 2009

Related U.S. Application Data

(63) Continuation-in-part of application No. PCT/EP2006/009217, filed on Sep. 20, 2006.

(51) Int. Cl.
*A01H 5/00* (2006.01)
*A01H 5/10* (2006.01)
*A01H 5/12* (2006.01)

(52) U.S. Cl. ...................................................... 800/305

(58) Field of Classification Search ........................ None
See application file for complete search history.

(56) References Cited

U.S. PATENT DOCUMENTS

2005/0144672 A1* 6/2005 Knerr ............................ 800/305

OTHER PUBLICATIONS

F. Benoit, et al., Effect of a Photoselective Greenhouse Film on a Few Vegetable Crops in the Belgian North Sea Climate, 14th International Congress on Plastics in Agriculture, Tel Aviv, Israel, Mar. 1997, p. 81-92.
Matthew D. Kleinhenz, et al., Variety, Shading, and Growth Stage Effects on Pigment Concentrations in Lettuce Grown Under Contrasting Temperature Regimens, Horttechnology (2003) vol. 13, No. 4, p. 677-683.
Donald T. Krizek, et al., Inhibitory Effects of Ambient Levels of Solar UV-A and UV-B Radiation on Growth of c. New Red Fire Lettuce, Physiologia Plantarum (1998) vol. 103, p. 1-7.
I. Voipio, et al., Responses of Red-Leaved Lettuce to Light Intensity, UV-A Radiation and Root Zone Temperature, Acta Horticultuae (1995) vol. 399, p. 183-187.

* cited by examiner

*Primary Examiner* — Eileen B O Hara
(74) *Attorney, Agent, or Firm* — Vedder Price P.C.; Thomas J. Kowalski; Deborah L. Lu

(57) ABSTRACT

The present invention relates to a head-forming lettuce plant of the species *Lactuca sativa* having red leaves throughout the head, including the heart. The red leaves in the heart are red even in the absence of radiation with wavelengths shorter than 400 nm, wherein the absence of radiation with wavelengths shorter than 400 nm is in the growing environment during the complete period from sowing until observation. The ratio between anthocyanin and chlorophyll is between 4 and 50, preferably between 9 and 27. The invention also relates to progeny of the plant.

24 Claims, 14 Drawing Sheets

RED LETTUCE

CROSS-REFERENCE TO RELATED APPLICATIONS

This application is a continuation-in-part of International application no. PCT/EP2006/009217, filed Sep. 20, 2006, published as WO 2007/039137 on Apr. 12, 2007, and claiming priority to EP 05077135.1, filed Sep. 20, 2005.

All of the foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates to a red lettuce plant, to the head of lettuce that can be obtained therefrom and to the gene complex that is responsible for the red colour of the lettuce.

BACKGROUND OF THE INVENTION

Lifestyles change and the demand from restaurants and catering firms for colourful and interesting garnish and even from the housewife for ready-to-use processed salads continue to rise. As a result, the breeding companies are looking for varieties with prominent colour, better taste and a wide variety of texture. The lettuce market can be divided into three groups, namely entire whole heads, pre-cut whole heads and baby leaves.

At present the attractive red colour in pre-cut lettuce mixtures is often provided by the presently available "red" lettuce (*Lactuca sativa*), or by radicchio rosso (*Cichorium intybus*), red cabbage or red chard. The "red" lettuce that has been known so far is not really red throughout the leaves. In particular the head forming types are either only red along the leaf edges or speckled with red. They are never completely red in the heart. This is caused by the fact that the red colour is only expressed in those parts of the head that are exposed to daylight, more specifically to UV-radiation. Leaves of the so-called "red" lettuces are therefore for the main part green and their red does hardly contribute to the red colour impression of a pre-cut lettuce mixture.

Often the transitional stage between the red part and the green part of the leaf is brown-coloured. This brown colour is considered as visually unattractive. Red speckled lettuces are associated with plant diseases or bloodstains. At present plant breeders select against the brown colour as well as against the speckled red colouring. In addition, it is even found that speckled or brown coloured lettuce leaves are often discarded, both in the lettuce packaging industry and by the consumer.

The disadvantage of using leaves from other vegetables than lettuce is that the different taste of these other vegetables is often experienced as undesirable. Radicchio rosso is for example a *Cichorium intybus* that has a bitter taste. The texture of red cabbage is entirely different from the much softer texture of lettuce.

Anthocyanin synthesis in lettuce is induced by UV-radiation (see for example Voipio & Autio, 1995, Responses of red-leaved lettuce to light intensity, UV-A radiation and root zone temperature. In: Acta Horticulturae 399. Greenhouse environmental control and automation. Eds. B J Bailey, T Takakura. Kyoto, Japan. p 183-187; Benoit, et al., 1998, Effect of a photoselective greenhouse film on a few vegetable crops in the Belgian North Sea climate. In: 14th International congress on plastics in agriculture, Tel Aviv, Israel, March 1997. Laser Pages Publishing, Jerusalem, Israel. p 81-92; Krizek et al., 1998, Inhibitory effects of ambient levels of solar UV-A and UV-B radiation on growth of cv. New Red Fire lettuce. Physiologia Plantarum 103(1), p 1-7; Kleinhenz et al., 2003, Variety, shading, and growth stage effects on pigment concentrations in lettuce grown under contrasting temperature regimens. Hortechnology 13(4), p 677-683). The development of a red colour in many plant species is dependent on the production of anthocyanin.

The many different varieties of lettuce are often grouped into three types. The most common is head lettuce of which there are the crisp head (or iceberg) and butter head. Romaine lettuce (or cos lettuce) forms a loose upright head. The "leaf" lettuce types are non-heading and loose leafed.

In head-forming lettuce types the heart of the head is to a more or lesser extent closed and cannot be reached by light. It is thus not possible to have anthocyanin production in closed heads such as iceberg lettuce and butter lettuce or in romaine lettuce, which has a loosely closed head.

A related problem is the lack of red colouration of red lettuce grown in glasshouses, plastic tunnels, or in closed containers. Due to the lack of UV-radiation, which is reflected by the glass or plastic covering or which is lacking in the artificial assimilation light spectrum, the expression of anthocyanin is much less than in outdoor conditions. This reduces the possibilities to produce red lettuce under indoor conditions, and therefore the possibility to produce red lettuce protected from adverse weather conditions, like cold, heat, and all sorts of precipitation.

SUMMARY OF THE INVENTION

The present invention now provides a red lettuce, having red leaves throughout the head, including the heart. The heart leaves of red lettuce of the invention are in essence completely red, which means that they contain a uniquely high anthocyanin/chlorophyll-ratio. This is very surprising because light, more specifically UV-light, which is deemed necessary for the synthesis of anthocyanin is not able to penetrate into the heart of the head. This demonstrates that in the lettuce of the invention a light-independent mechanism is responsible for the production of anthocyanin.

This light-independency also allows for the cultivation of red lettuce, headed or non-headed, under glass or plastic or in closed containers. The latter uses artificial assimilation lighting which usually gives problems with the development of red colour. This is due to the fact that the UV-wavelengths (280-400 nm) which are normally essential for induction of anthocyanin synthesis, are more or less lacking in the light spectrum.

Under glass or plastic a similar lack of UV-radiation is commonly caused by strong UV-interception of the covering. However, due to its UV-independent anthocyanin expression the red lettuce of the invention is suitable for glasshouse, plastic house, and closed container cultivation. This is due to the light-independent mechanism of the present invention, which will also be indicated as "UV-independent anthocyanin expression", or "UV-independent red colouration".

The Deposits with NCIMB, under deposit accession numbers NCIMB 41337, NCIMB 41338 and NCIMB 41339 were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The present invention will be further illustrated in the non-limiting examples that follow and that refer to the following figures.

DETAILED DESCRIPTION

Figure 1:
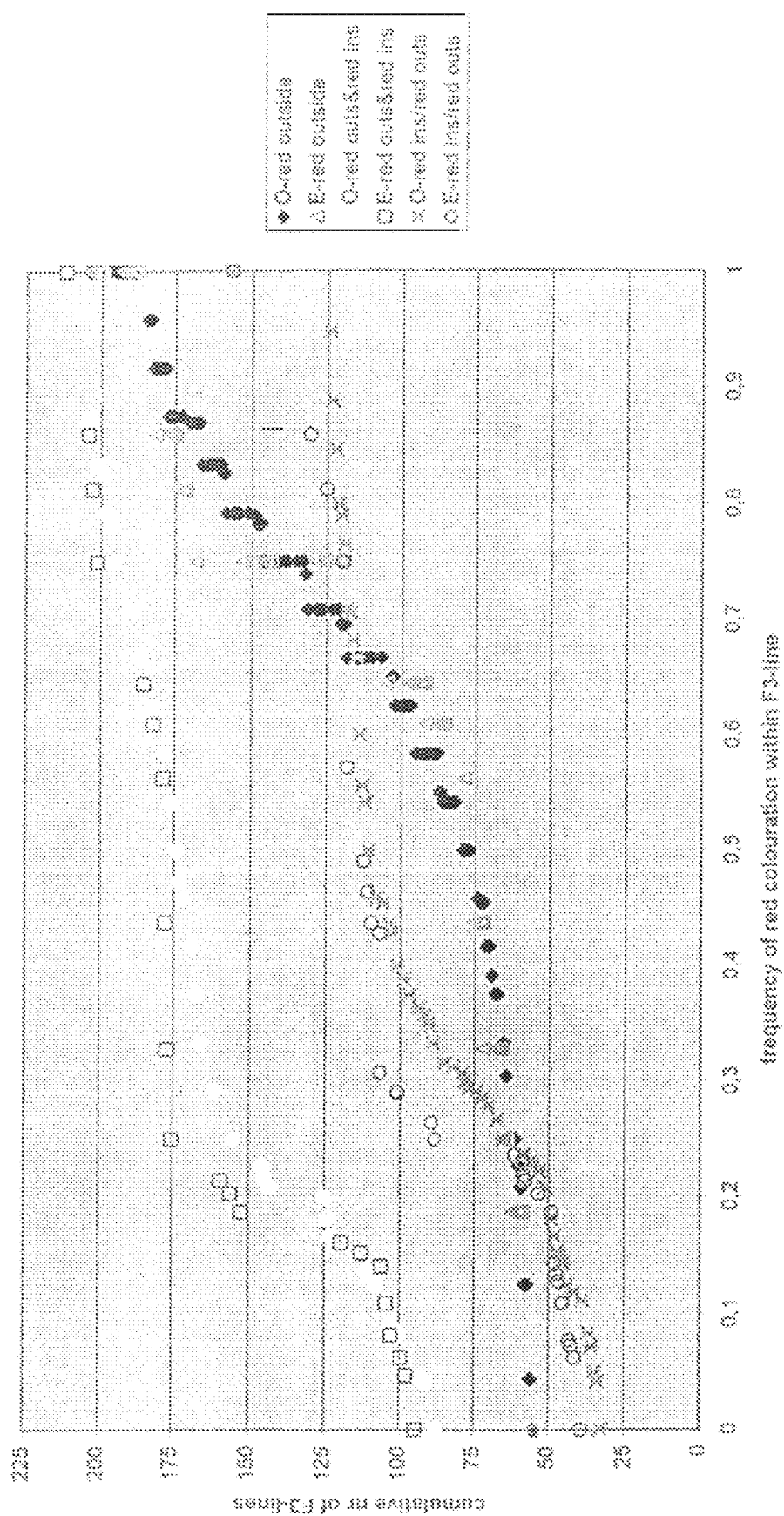
FIG. 1 is a graph that shows the distribution of within-line segregation of red colouration of outer and inner leaves for population of 212 F3-lines obtained from cross '99P.30637× cv. 'Sharp Shooter'.

In a particular embodiment of the invention, the absorbance ratio A523/A665 between anthocyanin and chlorophyll is between 4 and 50, preferably between 9 and 27.

Whether the expression of anthocyanin in the present invention is completely independent of UV-radiation, or that it is triggered by much lower levels of UV-radiation than normally required for anthocyanin expression in regular red lettuce plants, is not completely known yet. However, for practical usefulness of the invention this difference does not matter.

Although the invention is particularly useful in head-forming lettuce types, the light-independent red colouring of the invention can also be used in other lettuce types such as leaf lettuce and in baby-leaf production, which is the production of young lettuce plants for harvesting small, immature leaves.

The pedigree of a red lettuce of the invention is given in Example 1.

The invention relates to all progeny of the original parents that have red leaves in the heart of the head and that meet one or more of the other requirements of the invention, such as the ratio between chlorophyll and anthocyanin of the heart leaves.

In addition, non-heading, loose leaf or baby lettuce plants that have the UV independent red colouration of the invention are also considered progeny of the completely red head-forming lettuce plants and thus part of this invention.

The selection of lettuce plants that already are or can lead to the lettuce plants of the invention can be based on visual selection of red-coloured young plants (step 1). Growing them under glass or plastic can subsequently distinguish between UV-dependent anthocyanin expression, i.e. poor red colouration, and UV-independent anthocyanin expression, i.e. a relatively strong red colouration. These latter plants are planted and grown until they are headed. Then visual selection of plants with red heart leaves is performed by cutting the top off each plant. The red-hearted plants are then selected to produce offspring seed.

Crosses are chosen to increase the level of red colouration, and/or to obtain the required level of heading of the mature plant.

As used herein, a lettuce plant is defined as headed, when it has got an 'open head' or a 'closed head', according to the guidelines of UPOV for the characteristic 'head formation' ('TG/13/9. Lettuce (*Lactuca sativa* L.) Guidelines for the conduct of tests for distinctness, uniformity and stability.' International Union for the Protection of New Varieties of Plants. Geneva. 2004).

The lettuce hearts of the present invention have an absorbance ratio A523/A665 between chlorophyll and anthocyanin which is preferably higher than 9, more preferably 13 or higher. In normal red lettuce this ratio was never found to be higher than 3. The chlorophyll and anthocyanin concentrations used in determining the ratio of the invention are determined by means of spectrophotometry. Sample preparation and analysis is presented in Example 2.

It is to be noted that anthocyanin levels as high as in the heart leaves of the present invention can possibly be found in other lettuce varieties, which are non-heading. Some examples of such non-heading varieties are 40-0203103-B (Knerr L D, 2005. Lettuce cultivar 40-0203103-B. US Patent application US 2005/0144672 A1), Galactic, New Red Fire, Rolina (Kleinhenz et al, 2003. Variety, shading and growth stage effects on pigment concentrations in lettuce grown under contrasting temperature regimens. Horttechnology 13(4) p. 677-683), Red Salad Bowl, and Sesam (Voipio I. and Autio J., 1995. Responses of red-leaved lettuce to light intensity, UV-A radiation and root zone temperature. Acta horticulturae 399. p. 183-187).

However, these varieties have heart leaves with very high chlorophyll levels, in comparison with the heart leaves of the present invention, as a result of high light exposure due to the non-heading characteristic. On the other hand, heading varieties can possibly be found with similarly low chlorophyll levels in the heart leaves as in the heart leaves of the present invention. However, the heart leaves of these heading varieties do not show the high anthocyanin levels in comparison with the heart leaves of the present invention. Due to the low light exposure of the heart leaves anthocyanin synthesis is normally poorly induced. In the present invention, the anthocyanin production is UV-independent. This explains why the anthocyanin/chlorophyll-ratio of the present invention is on a unprecedentedly high level.

This new form of red colouration that is UV-independent is found and developed in headed lettuce plants and differs from the red colouration as presented in the prior art. However, the invention also relates to non-headed lettuce plants, such as loose leaf or baby leaf lettuce plants or lettuce plants that are grown in glass houses or under plastic where the amount of UV is lower that have the feature "UV-independent red colouration" of the invention.

Red colouration of the heart leaves was also scored on the RHS colour chart (The Royal Horticultural Society, London, UK). Heart leaf lamina colour, especially on the top of leaf, of the present invention was scored as 183A, 184A, or 187B, all in the greyed-purple group. The colour of the rest of the leaf lamina was scored as 180B, 180C, 180D, or 181C, all in the greyed-red group.

It is also possible to score the red colouration and anthocyanin expression on plants grown under glass or plastic, i.e. conditions with reduced levels of UV-radiation, when compared to the light in outdoor conditions. Also here the plants of the present invention can show higher levels of anthocyanin and a darker red colour than regular red lettuce. Especially newly appearing leaves of the plants of the present invention are much more red than the newly appearing leaves of common red lettuce plants.

A genetic analysis of the red lettuce of the invention was performed as described in Example 2. It was found therein that at least three genes are involved in the red colouring of the heart of the head.

The present invention thus relates to lettuce plants that are capable of expressing anthocyanin and have in addition at least the three genes that are involved in the red colouring of the heart of the head. Preferably, a plant of the invention comprises the complete gene complex described in Example 2.

It is possible to assess the presence of the loci involved in red coloration of the present invention by closely linked DNA-markers, like AFLP, RFLP, RAPD, SCAR, CAPS, SSR, or SNP. For instance, a marker-trait linkage analysis in the population mentioned above, and its offspring can provide such closely linked DNA-markers.

The presence in a lettuce plant of a similar genetic constitution of red colouration of the inner leaves as in the present invention, i.e. assessing whether a lettuce plant is a plant according to the invention can easily be assessed by comparison of the phenotype of such potential plant of the invention with the phenotype of a known plant of the present invention. The phenotype can be assessed by, for example, the red colouration of the inner leaves, the anthocyanin/chlorophyll-ratio of the heart leaves, and/or the red colouration of plants grown under glass or plastic.

Another way of assessing the similarity of the genetic constitution between a potential plant of the invention and a known plant of the invention is by comparison of the marker genotype of the potential plant with the marker genotype of a known plant of the present invention. The marker genotype is defined by a set of DNA-based markers, like AFLP, RFLP, RAPD, SCAR, CAPS, SSR, or SNP, which are closely linked to the loci which involved in the red expression of the present invention.

Another way of assessing the similarity of the genetic constitution, is the comparison of the genotype of a potential plant of the invention with the genotype of a known plant of the present invention. This genotype comparison is done on an F2-population, derived by self-fertilising an F1-plant from a cross between the potential plant and a known plant of the present invention. The F2-population can be investigated for absence of segregation for the phenotype, i.e. the red colouration of the inner leaves. In all comparisons phenotypes can also be assessed by, for example, the anthocyanin/chlorophyll-ratio of the heart leaves, or the red colouration in plants grown under glass or plastic.

Seed of red lettuce plants according to the invention was deposited with the NCIMB on 18 Jul. 2005 under accession numbers NCIMB 41337, NCIMB 41338 and NCIMB 41339.

The invention also relates to progeny of these seeds, as well as to plants that have obtained the genetic constitution or gene complex of plants of the invention that leads to the red colouring according to the invention, either by crossing or by means of molecular biological techniques. The invention also relates to the progeny of these plants that have maintained or acquired the trait of red colouring of the invention.

To transfer the genes that are responsible for the red colour to another plant backcross breeding can be used. For this a desirable homozygous cultivar or inbred is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent (red colouring of the leaves in the heart) are selected and repeatedly crossed (backcrossed) to the recurrent parent. The resulting plant is expected to have the attributes of the recurrent parent (e.g., cultivar) and the desirable trait transferred from the donor parent. In case the inheritance of the red colouration is more complex than the inheritance of the other desired trait, or combination of traits, the parent with red-coloured heart leaves can be used as recurrent parent, and the parent with the other desired trait, or combination of traits, can be used as donor parent. Descriptions of other breeding methods that are commonly used for different traits and crops can be found in one of several reference books (e.g., "Principles of Plant Breeding" John Wiley and Son, pp. 115-161, 1960; Allard, 1960; Simmonds, 1979; Sneep et al., 1979; Fehr, 1987).

Figure 2:
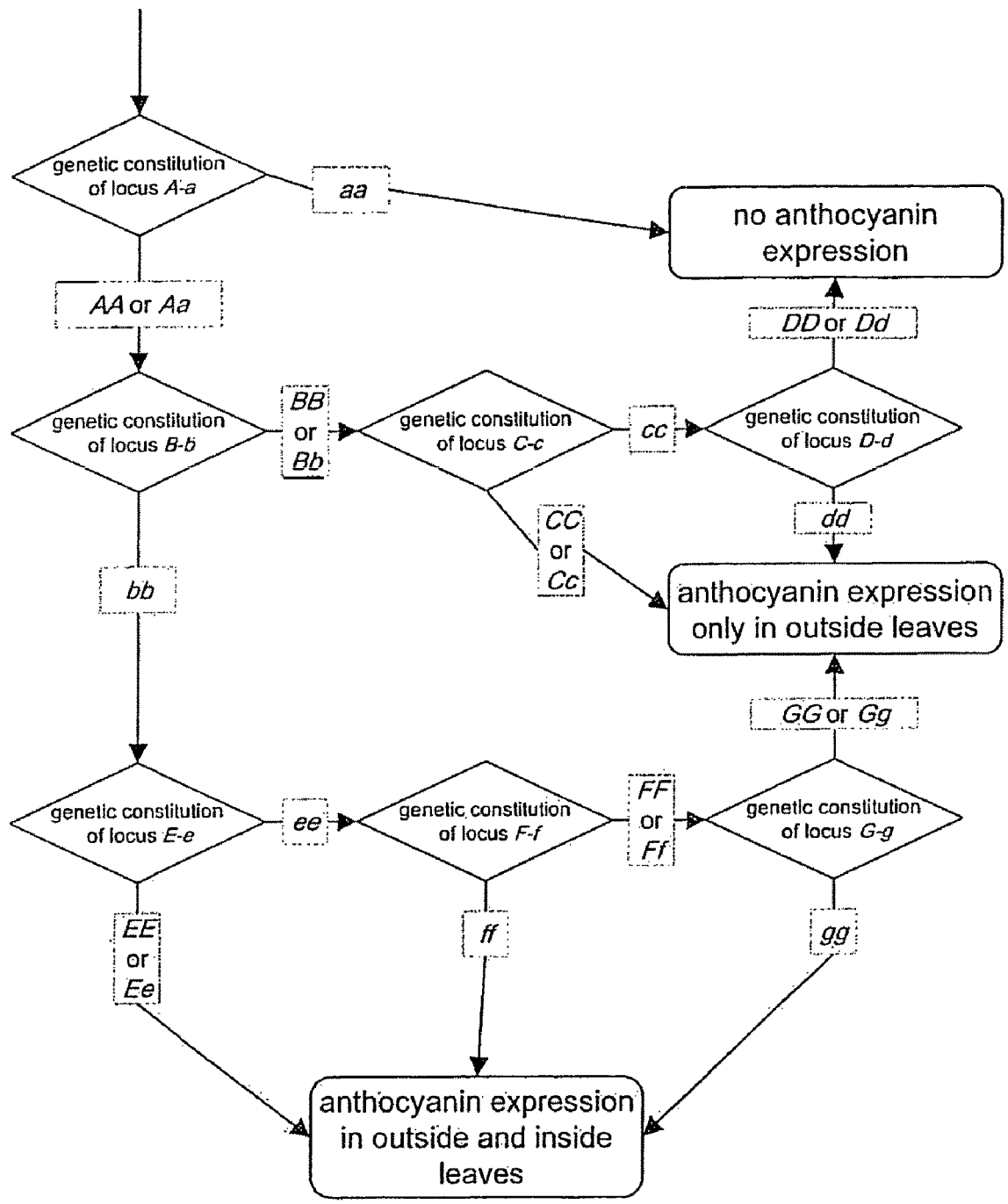
FIG. 2 is a diagram that shows the genetic model for anthocyanin expression based on segregation in cross '99P.30637'×cv. 'Sharp Shooter'.

In greater detail, FIG. 1 shows distribution of within-line segregation of red colouration of outer and inner leaves for population of 212 F3-lines obtained from cross '99P.30637'× cv. 'Sharp Shooter'. Three classifications of red colouration were applied on the population: 'red outside', i.e. within-line frequency of plants with red outer leaves, irrespective of inner leaf colour; 'red outs&red ins', i.e. within-line frequency of plants with red outer and red inner leaves, 'red ins/red outs', i.e. frequency of plants with red inner leaves within the line-total of plants with red outer leaves. O=observed; E=expected, according to genetic model FIG. 2 shows the genetic model for anthocyanin expression based on segregation in cross '99P.30637'×cv. 'Sharp Shooter'.

Figure 3A:
FIGS. 3A-3F show representative examples of young plants from the lines 03P82421, Pierrot, Pippo, Gringo, Apache and Bijou, respectively.
Figure 3B:
Figure 3C:
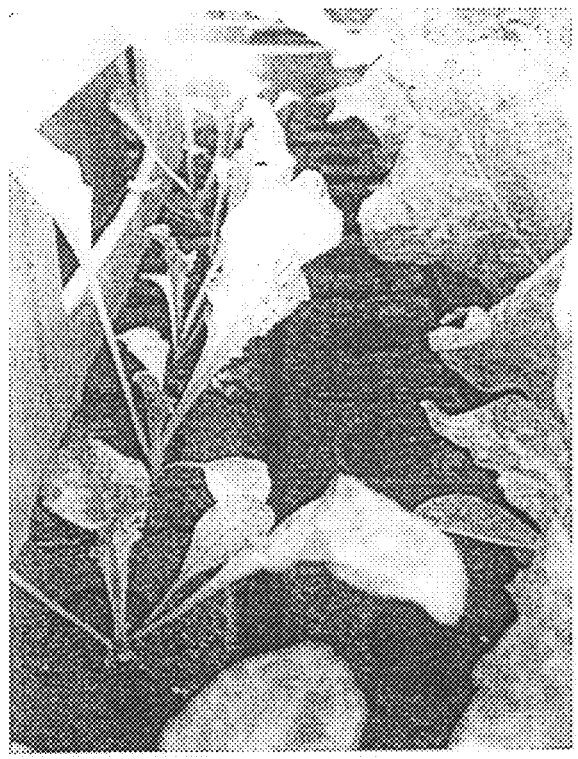
Figure 3D:
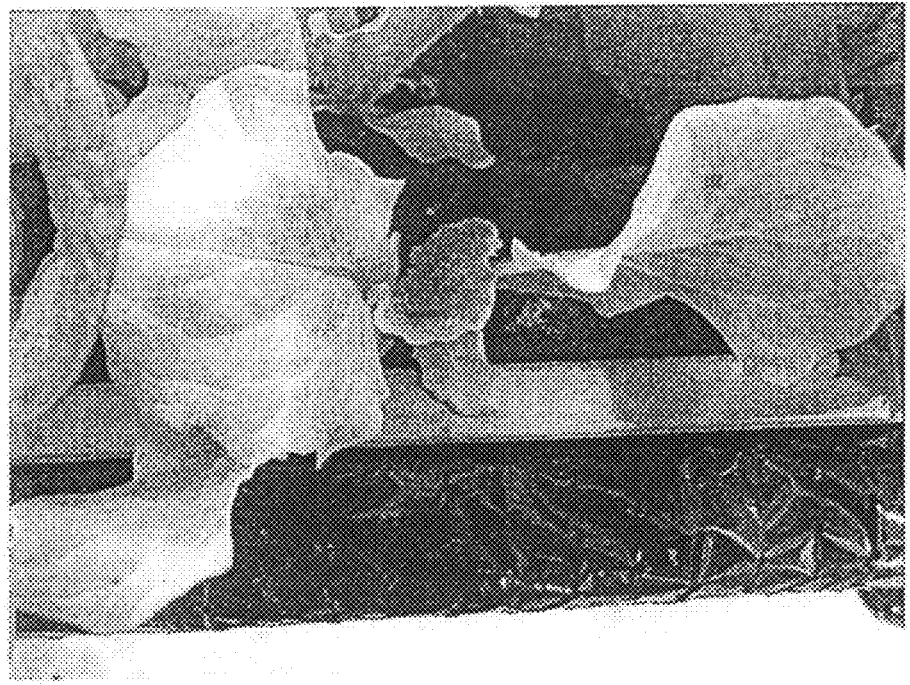
Figure 3E:
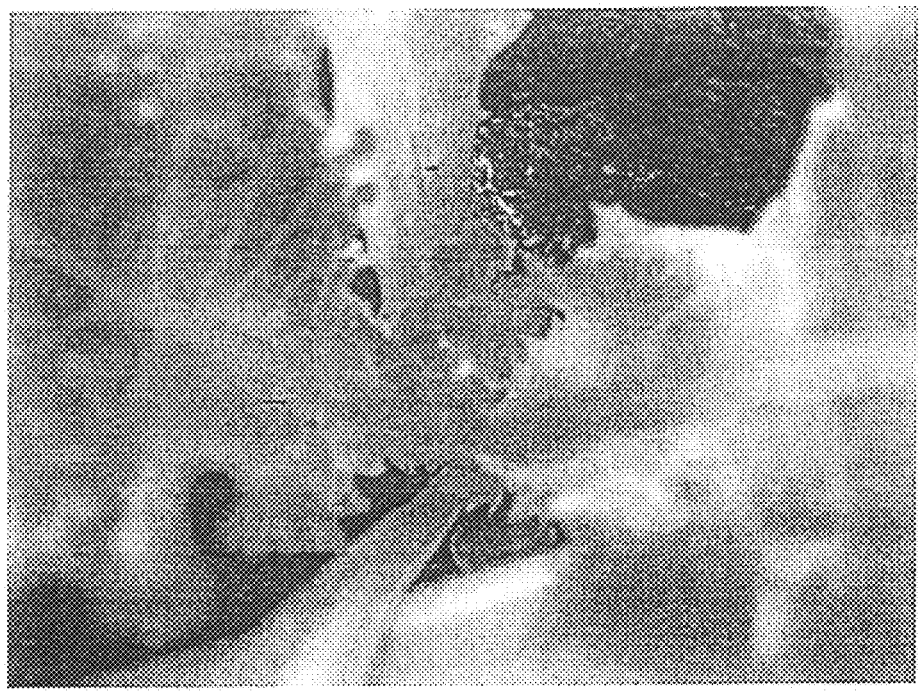
Figure 3F:
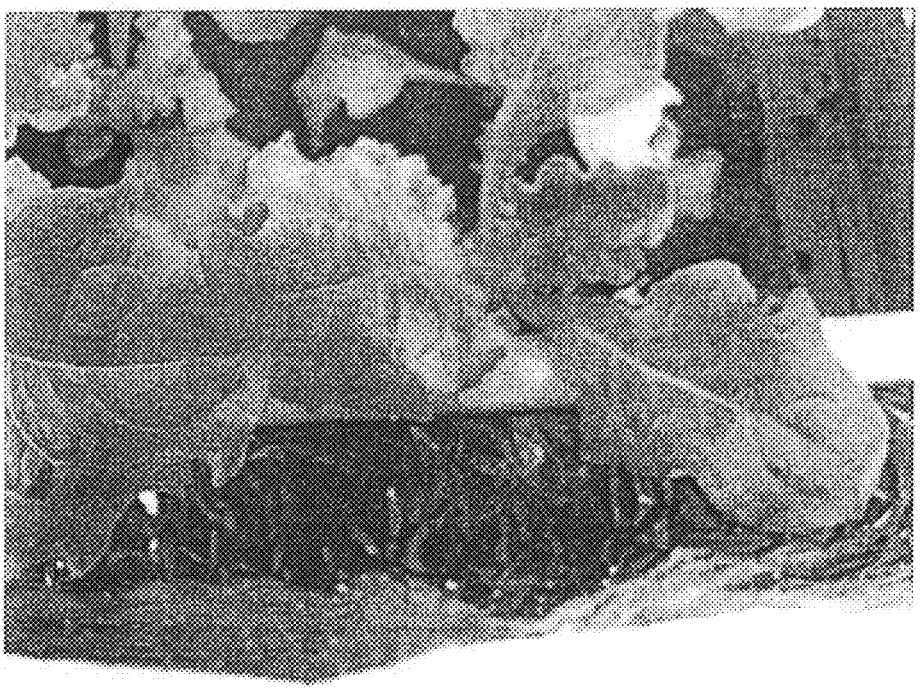

FIG. 3a shows a plant of the invention. This young plant is a plant from a seed from the line 03P82421, which was obtained after three generations of self fertilisation of plant 99P38154. FIGS. 3b, 3c, and 3d show young plants of parents Pierrot, Pippo, and Gringo, respectively. FIGS. 3e and 3f show young plants of comparison varieties Apache and Bijou, respectively. All these young plants were grown on peat blocks in a growth chamber with 14 h light at 16° C. and 10 h dark at 12° C. Light was produced by Philips TLD 36 W 840 REFLEX tubes, with 1 tube per 0.24 square m, at 0.6 m distance above the plants.

Figure 4:
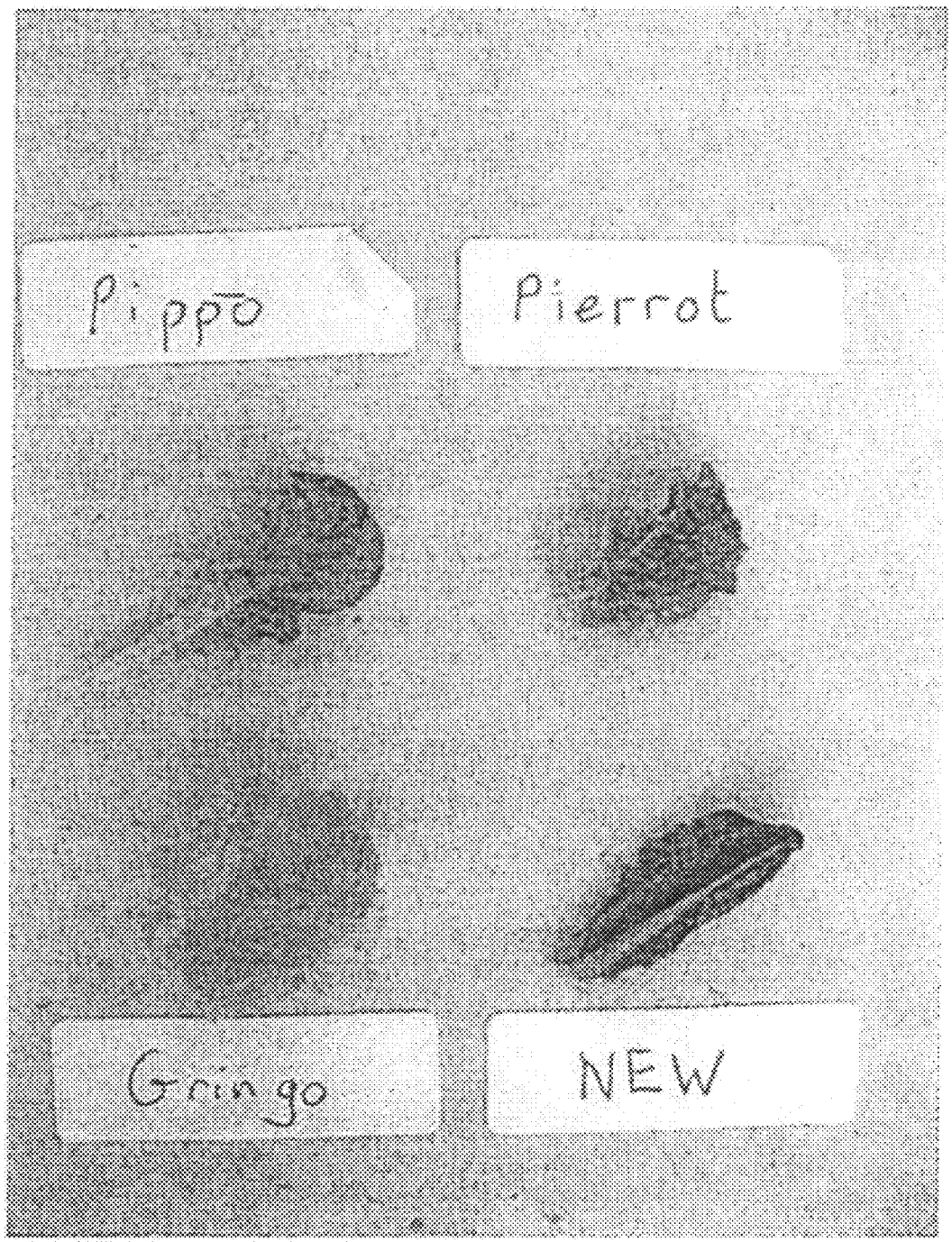
FIG. 4 shows a comparison of representative examples of a young leaf from a plant of the present invention with young leaves from varieties Pippo, Pierrot and Gringo.
Figure 5A:
FIGS. 5A-5D show a comparison of representative examples of a plant of the invention (01P80164) and the variety Darkland (99R10044).
Figure 5B:
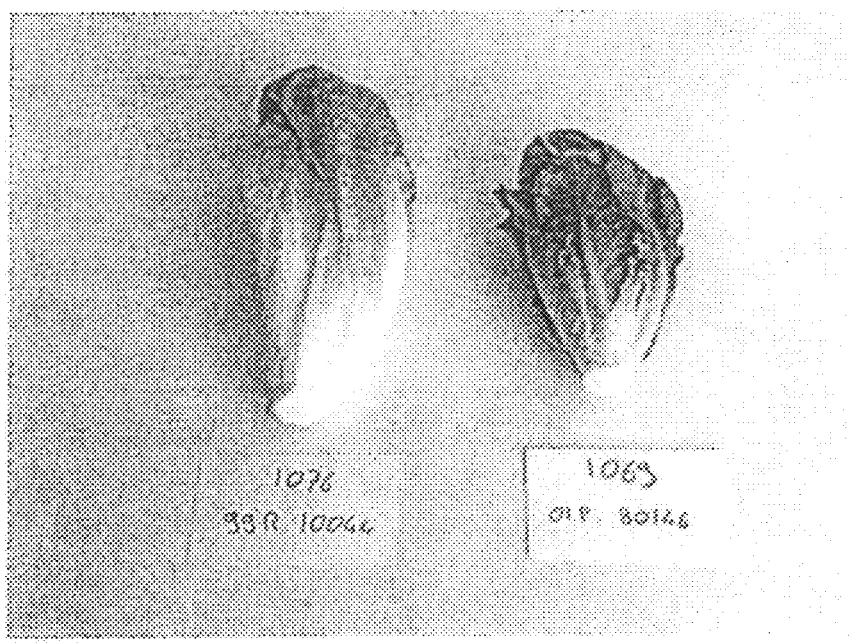
Figure 5C:
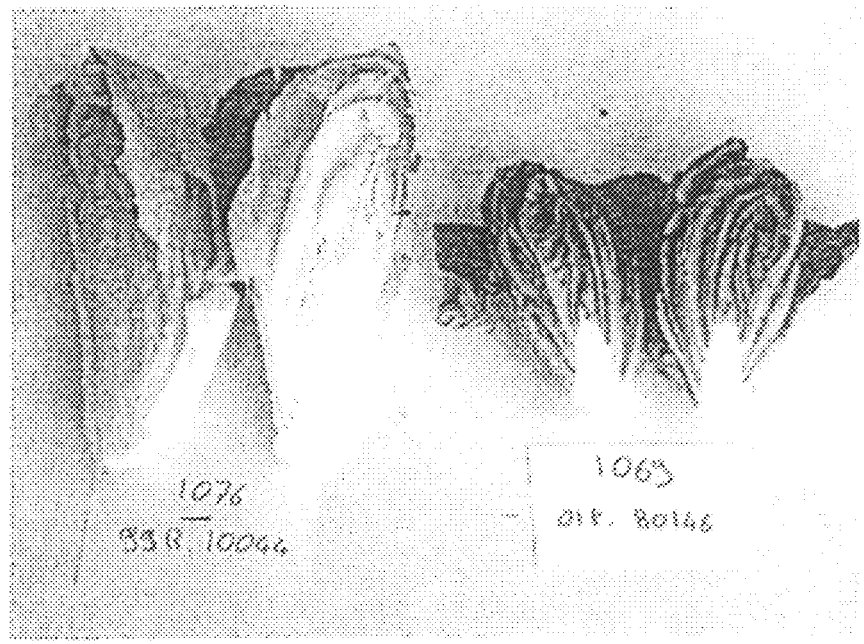
Figure 5D:
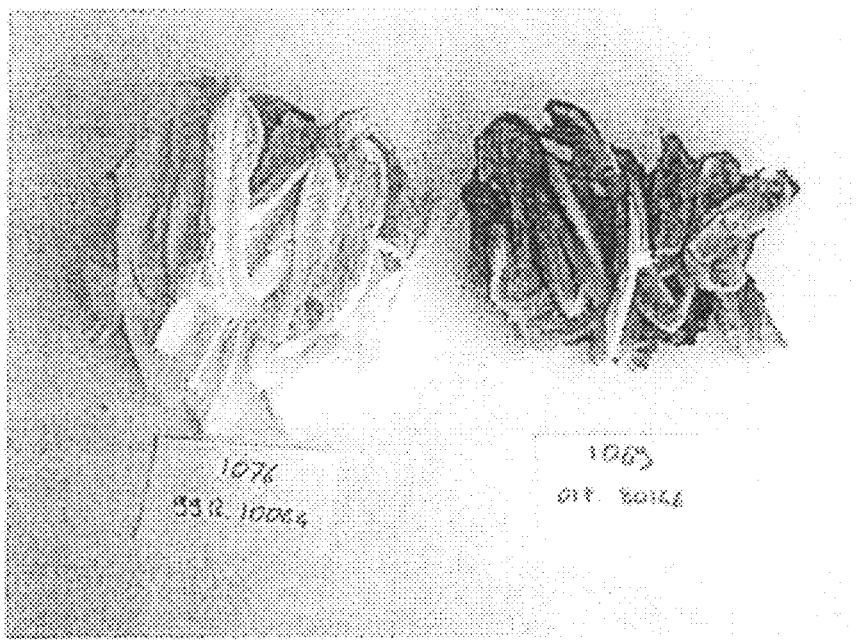
Figure 6A:
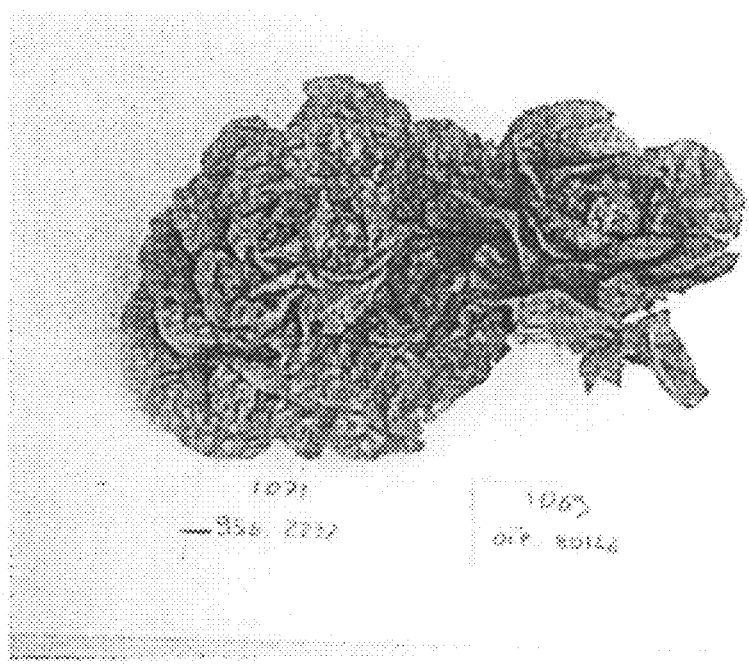
FIG. 6A-6D show a comparison of representative examples of a plant of the invention (01P80164) and the variety Pierrot (95G2237).
Figure 6B:
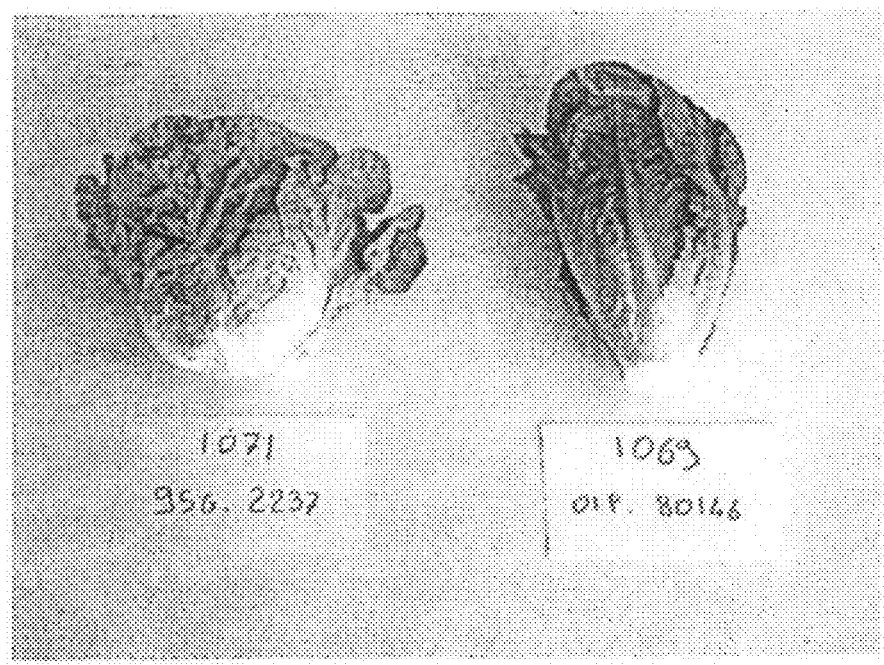
Figure 6C:
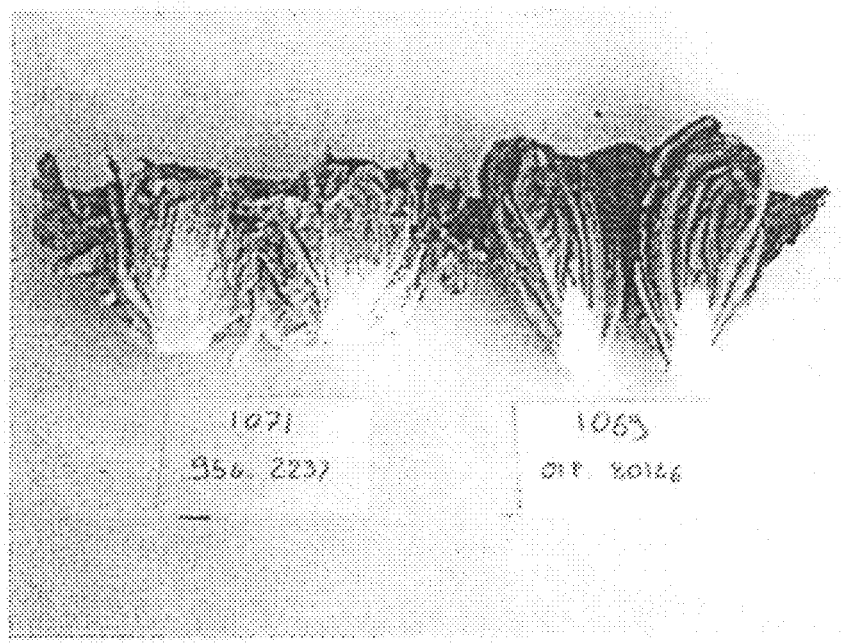
Figure 6D:
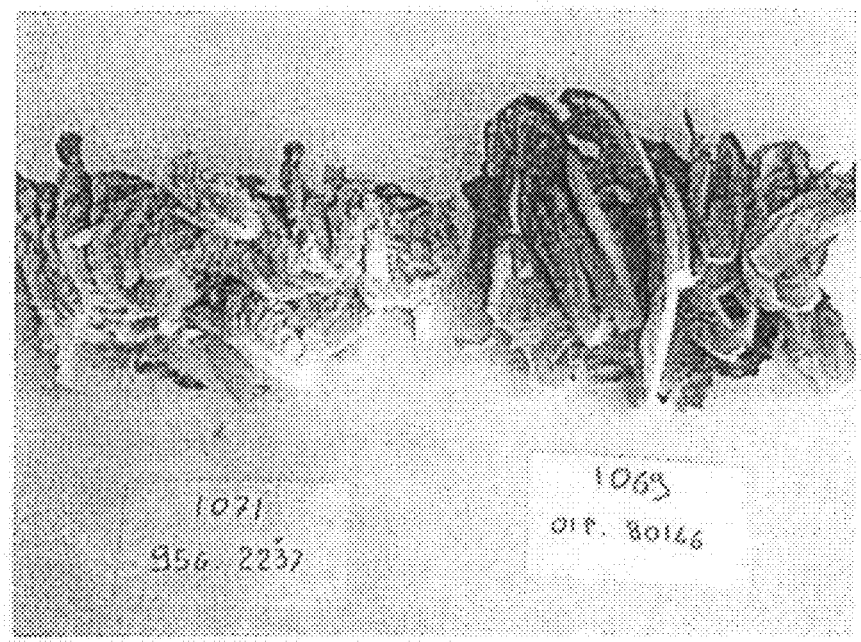
Figure 7A:
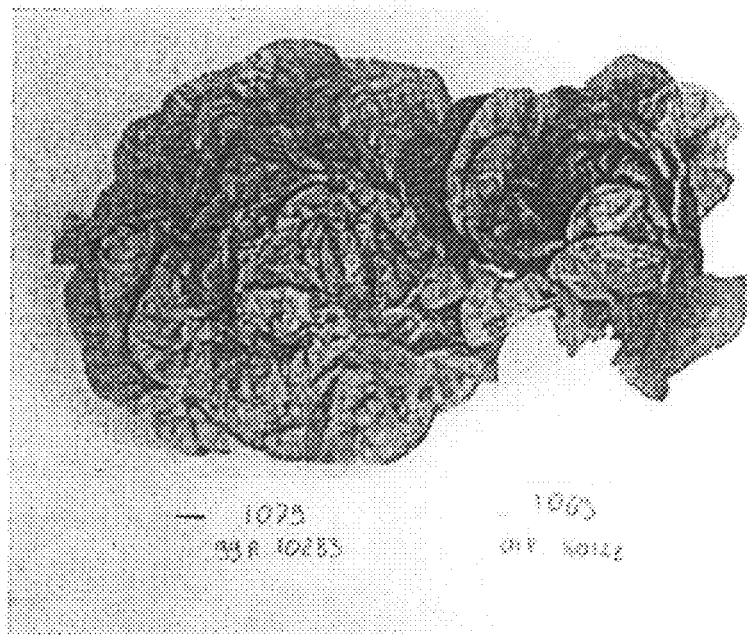
FIG. 7A-7D show a comparison of representative examples of a plant of the invention (01P80164) and the variety Roxy (99R10283).
Figure 7B:
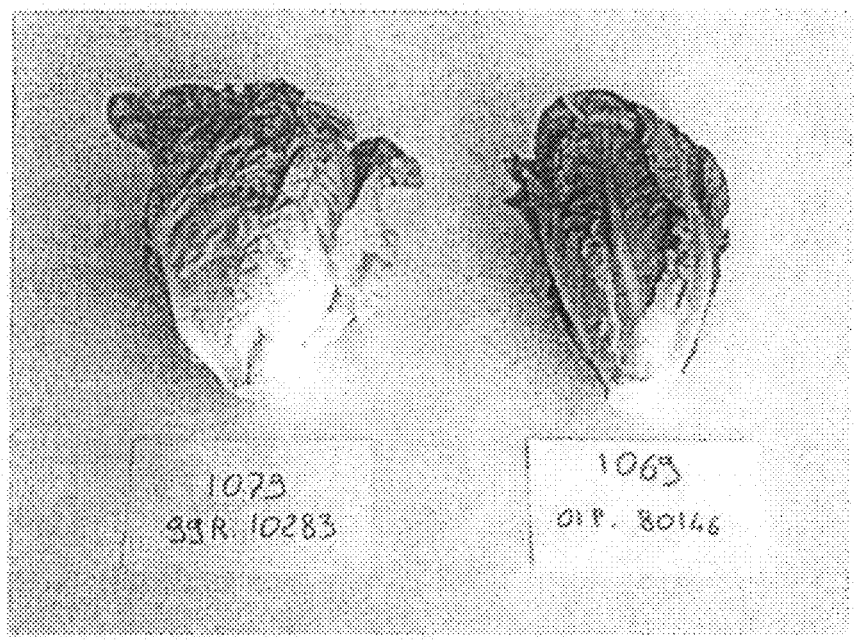
Figure 7C:
Figure 7D:
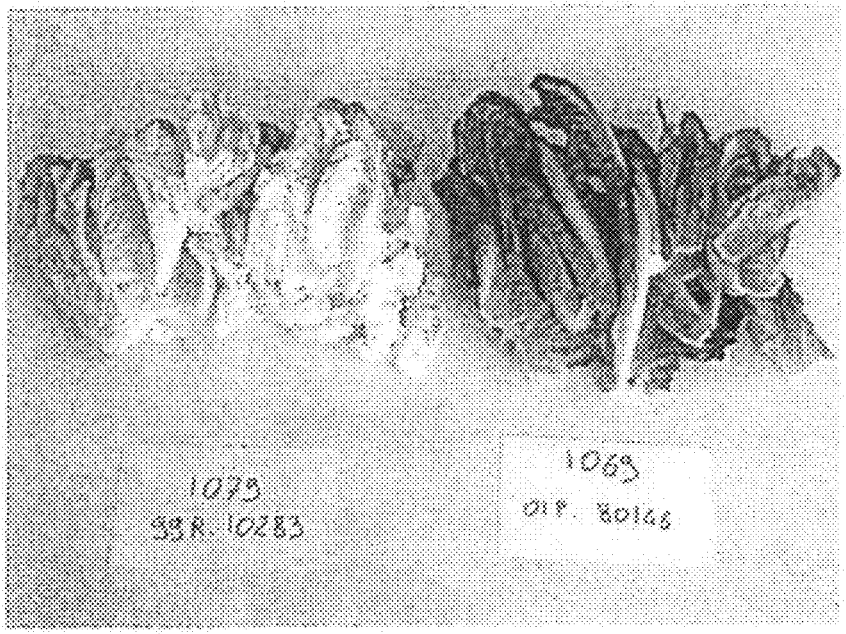
Figure 8A:
FIG. 8A-8D show a comparison of representative examples of a plant of the invention (01P80164) and the variety Sierra (95G1986).
Figure 8B:
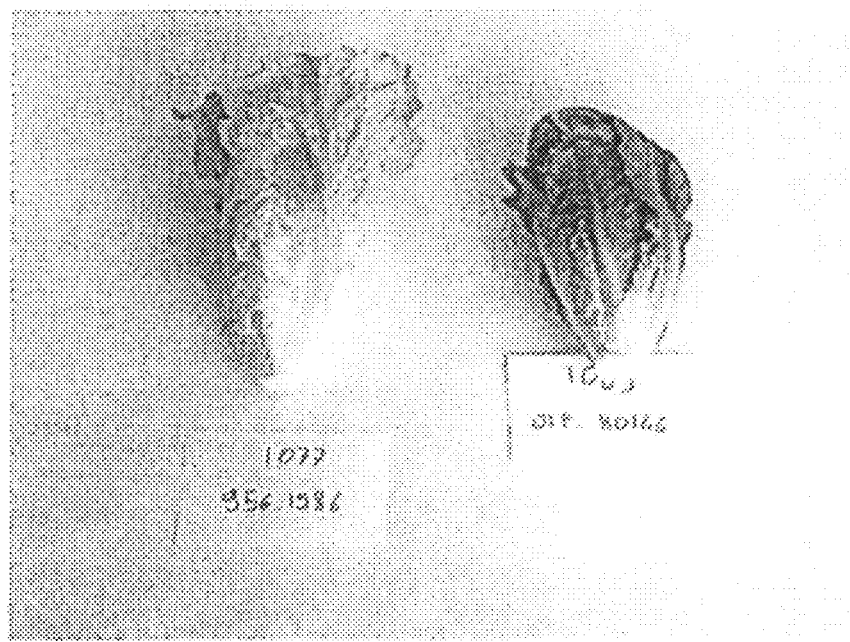
Figure 8C:
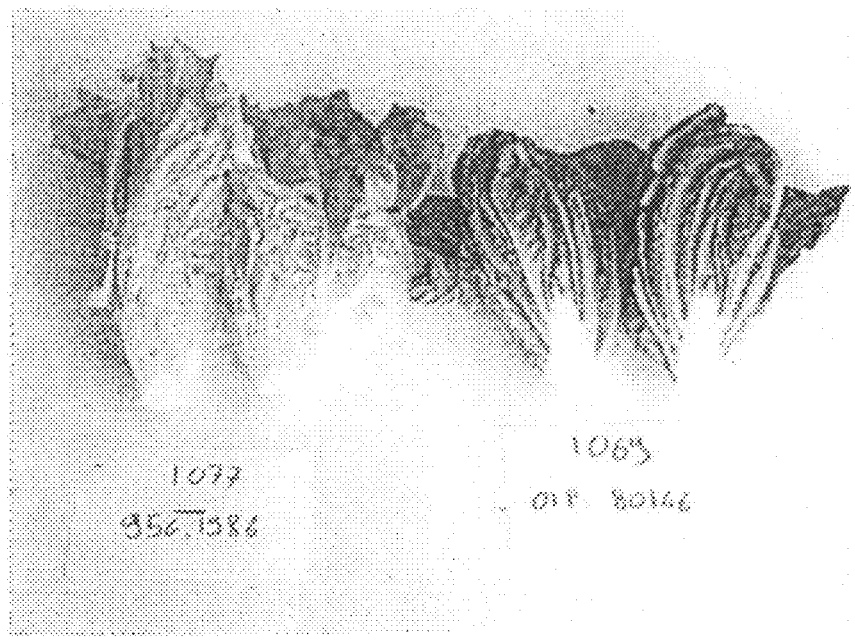
Figure 8D:
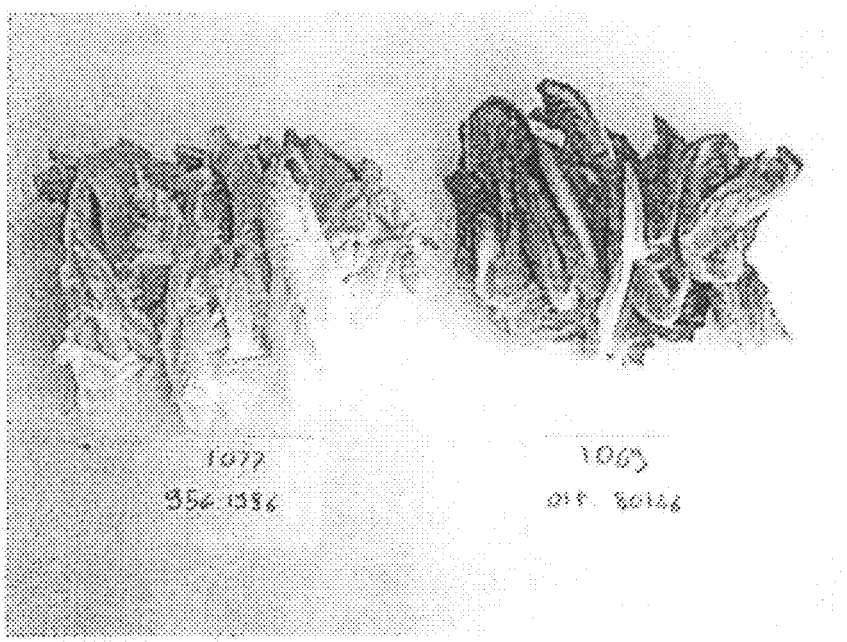

FIG. 4 shows a young leaf of a plant of the invention, indicated by 'NEW', in comparison to young leaves from the commercial varieties Pippo, Pierrot and Gringo. These young plants were grown on peat blocks in a growth chamber with 14 h light at 16° C. and 10 h dark at 12° C. Light was produced by Philips TLD 36 W 840 REFLEX tubes, with 1 tube per 0.24 square m, at 0.6 m distance above the plants.

FIGS. 5-8 show comparisons between a plant of the invention (01P80146) and the commercial varieties Darkland (indicated by '99R10044'; FIGS. 5a-5d), Pierrot (indicated by '95G2237'; FIGS. 6a-6d), Roxy (indicated by '99R10283'; FIGS. 7a-7d) and Sierra (indicated by '95G1986'; FIGS. 8a-8d), respectively. The a-figures (5a, 6a, 7a, 8a) are showing the full harvested heads, The b-figures (5b, 6b, 7b, 8b) are showing the heart without outer leaves, The c-figures (5c, 6c, 7c, 8c) are showing a longitudinal section of the heart. The d-figures (5d, 6d, 7d, 8d) are showing cut heart leaves. The lettuce plants of the invention are completely red in the heart of the head whereas the other lettuce plants are not. All plants are grown in Aramon, France in 2002: sown on 10 Jan. 2002, transplanted into a confidential open field on 15 Feb. 2002, harvested on 25 Apr. 2002.

EXAMPLES

Example 1

Pedigree of a Red Lettuce of the Invention

The lettuce of the invention was obtained according to the following pedigree: in 1986 a cross was made between a plant of cv. Pippo (Rijk Zwaan; red-coloured) and a plant of cv. Blonde Maraichere (Caillard; green-coloured).

In 1988 a red offspring plant from this cross was used as a father in a cross with a plant of cv. Gringo (Rijk Zwaan; red-coloured). In the same year a cross was made between a plant of cv. Pierrot (Rijk Zwaan; red-coloured) and a plant of cv. Roxette (Rijk Zwaan; green-coloured).

In 1989 a red offspring plant from this cross was used as a father in a cross with a plant of cv. Krizet (Rijk Zwaan; green-coloured).

In 1992 a red F3-offspring plant was selected from the Krizet×(Pierrot×Roxette)-cross mentioned above and it was used as a mother in a cross with a father plant, which was a selected red offspring plant from the Gringo×(Pippo×Blonde Maraichere)-cross mentioned above. A red F4-plant from this newly obtained 1992-cross was selected in 1995 and used as a mother in a cross with a plant of cv. Roxette (Rijk Zwaan; green-coloured).

Selection on type, heading, and colour, which was performed in the F2-, F3-, and F4-generation from this cross, resulted in a red F4-plant (98P.31582) in 1998. The F5-line appeared to be segregating for colour (red vs. green), but selection in the next generation resulted in three headed F5-plants with completely red heart leaves (99P.38152; 99P.38154; 99P.30637), which were multiplied in the years afterwards.

The offspring showed no segregating green plants, and seeds were deposited under nrs. 02R.2413, 01R.1439, 02R.2418. These F5-plants and their offspring have served as a parent source for further breeding of lettuce with light-independent red colouration.

In conclusion, it can be said that none of the used parent varieties, i.e. Pippo, Blonde Maraichere, Gringo, Pierrot, Roxette, and Krizet, have the characteristic red leaves in the heart of the head. The invention comprises the unique and new combination of genes from these red and green parent varieties, which is providing the completely red leaves in the heart of the head.

Example 2

Genetic Analysis of the Red Lettuce of the Invention

As used herein, a locus (plural: loci) is defined as the specific place on a chromosome where a gene is located. (Griffiths A J F, Miller J H, Suzuki, D T, Lewontin R C, Gelbart, W M. 'An introduction to genetic analysis.' 6$^{th}$ edition. 1996. WH Freeman and Company, New York.) The number of loci responsible for red colouration in a given plant can be established by a genetic analysis of the offspring of a cross of this plant with the green-coloured cv 'Sharp Shooter'.

A genetic analysis of the red lettuce of the invention was performed as follows: a cross was made between an offspring plant from F5-plant nr. 99P.30637, i.e. a plant of the present invention, and a non-brilliant green-coloured iceberg lettuce plant of cv. Sharp Shooter (S V S, Waycott et. al., 1999: U.S. Pat. No. 5,973,232). From the offspring of this cross 212 random F2-plants were multiplied into F3-lines.

These 212 F3-lines were evaluated in a confidential outdoor trial in Fijnaart, the Netherlands. Seeds were sown on peat blocks on Jun. 17, 2002, young plants were raised in a glasshouse, and transplanted in the field on Jul. 5, 2002. The harvest date (time of observation) was on Aug. 19 until Aug. 23, 2002. The plot size was 24 plants per F3-line, i.e. 4 rows of 6 plants. Lines were not replicated, because expression of colour traits is very stable within one trial. Observations were done per F3-plant.

Observed traits were: a) colour, and, if red, its intensity and expression pattern on the outer leaves, b) colour, and, if red, its intensity and expression pattern on the inner leaves, c) degree of heading, d) in case of green outer leaves: scoring in 2 classes: brilliant or non-brilliant.

The intensity and expression pattern of the red colouration was scored, in increasing order, as: 1) tinged or blushed, i.e. light red colouration on the outer and inner leaf edges, or on the inner leaf base, 2) red spotted, 3) green spotted, i.e. green spots on red leaf surface, 4) fully red, i.e. intensely red coloured without spots, on the light-exposed part of the outer leaf parts, and, in case of inner leaves, throughout the inner leaf.

Heading was scored between 1) slightly open heading, like Romaine or cos lettuce, and 2) strong heading with clearly overlapping leaves, like iceberg lettuce.

Some plants in the trial died before harvest. Of the intended 5088 plants, i.e. 212×24, in total 5007 F3-plants reached harvestable stage and were scored (see Table 1).

All plants showed heading levels, which were at least comparable to Romaine or cos lettuce. Data showed a segregation of 55 fully green lines out of the total of 212. Out of the 157 lines that were having at least one plant with red colouration, 28 lines comprised of plants which were all showing anthocyanin expression on the outer leaves. Out of these 28 lines, 8 lines comprised of plants which were all showing anthocyanin expression on the heart leaves. The red-coloured plants out of 33 of the 157 lines with at least one red-coloured plant, were showing anthocyanin expression only in the outer leaves and not in the heart leaves. The red-coloured plants out of another 33 of the 157 lines were always showing anthocyanin expression on both the outer leaves as well as the heart leaves. The red-coloured plants out of the remaining 91 lines all showed anthocyanin expression in the outer leaves. However, these plants showed a within-line segregation of anthocyanin expression in the heart leaves. Not a single plant out of the 5007 plants showed anthocyanin expression in the heart leaves in combination with green-coloured outer leaves, which had no anthocyanin expression.

It is therefore concluded that one or more genes that result in anthocyanin expression in the outer leaves, are required for anthocyanin expression in the heart leaves. In the case of segregation between red and green, segregation ratios between red and green ranged from 23:1 to 1:22 for colouration of outer leaves. For inner leaves the segregation ratios between red and green colouration ranged from 18:1 to 1:23, excluding all plants with green outer leaves. Table 1 shows the within-line distribution of plants with red and green colouration of outside and inside leaves for a population of 212 randomly derived F3-lines from cross '99P.30637'×cv. 'Sharp Shooter'.

TABLE 1

|  | all plants with green outer leaves | part of plants with red outer leaves | all plants with red outer leaves |
|---|---|---|---|
| all plants with green inner leaves | 55 | 29 | 4 |
| part of plants with red outer leaves have red inner leaves | 0 | 75 | 16 |
| all plants with red outer leaves have red inner leaves | 0 | 25 | 8 |

These segregation data were used to construct a genetic model, under the assumption of independent Mendelian segregation ratios. It was found that at least three loci are involved in obtaining UV-independent anthocyanin expression in the inner leaves. The first locus, further indicated as A-a, is also found in known red lettuce and the dominant allele A is required in all cases to obtain expression of anthocyanin. Probably this locus is the C or G-locus (Robinson et al., 1983, The genes of lettuce and closely related species. In: Plant Breeding Reviews 1. Ed. J. Janick. p 267-293).

A second locus is found by fitting the model, further indicated as B-b, where the homozygous presence of recessive allele b results in anthocyanin expression of outer leaves in combination with A. Two more loci, further indicated as C-c and D-d, were found to be also involved in anthocyanin expression in the outer leaves. Either presence of at least one copy of the dominant allele C, or homozygous presence of the recessive allele d results in anthocyanin expression in the outer leaves, but only in the case that also at least one copy of allele A is present.

Three more loci, further indicated as E-e, F-f, and G-g, were found. To obtain UV-independent anthocyanin expression in the inner leaves the presence of at least one A-allele, and two b-alleles is required, in combination with either the presence of one copy of the dominant E-allele, or the homozygous presence of the f-allele, or the homozygous presence of the g-allele. So the presence of alleles for red colouration on at least three loci, namely A-a, B-b, and either E-e, F-f, or G-g, is required for UV-independent anthocyanin expression in the inner leaves. Furthermore, it is assumed that at least three, but probably all seven loci mentioned above are involved in the intensity of red colouring of the present invention.

Example 3

Determination of Colour, Anthocyanins and Chlorophylls in Lettuce

1. Sample Preparation and Analyses
A spectrophotometer UltrospecIII (Pharmacia), with the following specifications was used:
Monochromator: Czerny Turner with holographic diffraction grating (1200 lines/mm)
Wavelength accuracy: ±1 nm
Wavelength reproducibility: ±0.5 nm
Detector type: single solid state silicon photodiode
Bandwidth: 5 nm
2. Principle
The red colour (anthocyanins) and green colour (chlorophylls) are determined with an biochemical method. Two extracts are made, one for measuring the absorbance at 523 nm which is a measure for total anthocyanins and one for measuring the absorbance at 665 nm which is a measure for total chlorophylls (chlorophyll a and b).
3. Sample Preparation
The headed and mature lettuce plant is harvested and outer leaves are taken off, until the heart is left over. The heart of the lettuce is used for the analysis. The heart leaves should not have been exposed to direct sunlight before harvest, except for a small tip of the leaf (maximum 10%) on the top of the plant. A heart contains at least 10 leaves with a length of 1 cm or longer. The oldest leaves of the heart should be concave.

The hearts are put in plastic bags and frozen at <−70° C. After at least a few days in <−70EC the frozen hearts are pulverized with a sledgehammer. The fine sample is grinded in a Grindomix (GM 200, Retsch, 5" 3000 rpm followed by 5" 5000 rpm) using the free floating lid in presence of liquid nitrogen (sample should be kept frozen) to obtain a powder.

The powder is then placed in a tube and the tube with powder is chilled in liquid nitrogen and optionally stored at <−70° C. till analysis.
4. Analysis
Three gram of the powder are weighed into four tubes of 50 ml. Two tubes are used for the analysis of anthocyanins and two tubes for the analysis of chlorophylls.

For measurements of anthocyanins 1.0 M HCl in 50% methanol is immediately added to the two tubes. 5-10 ml/g sample is used dependent on the colour of the sample and extract. The used volume (ml) is noted. The sample solution is mixed by hand and put on ice. A part of the solution is put in a 1.5 ml eppendorf tube and the tube is centrifuged at 4° C., 13000 rpm for 4 min.

Spectra are measured with a spectrophotometer with a band width of 5 nm. A 1 cm cuvette is used.

The spectrum of 360-900 nm is measured and the absorbance at 523 nm (if necessary after dilution with extraction liquid) and the maximum wavelength ($8_{max}$) are determined. $8_{max}$ should be close to 523 nm.

Chlorophylls are measured by immediately adding 100% methanol to the two tubes. 5-10 ml/g sample methanol is used dependent on the colour of the sample and extract. The volume (ml) used is noted. The sample solution is mixed by hand and sonificated in an ultrasonic bath for 5 min at 'set degas'. A part of the solution is put in a 1.5 ml eppendorf tube and centrifuged at 4° C., 13000 rpm for 4 min.

The spectrum of 360-900 nm is measured and the absorbance at 665 nm (if necessary after dilution with extraction liquid) and the maximum wavelength ($8_{max}$) determined. $8_{max}$ should be close to 665 nm.

The A523 and A665 are corrected to represent the absorbance of a solution of 1 g fresh weight in 10 ml extraction volume. The corrected A523 and A665 are calculated with a correction for weighted sample (in g), extraction volume (in ml) and if necessary dilution using the following formula: Correction:

$$A_{corrected.} = \frac{A_{measured} * extr.\ \text{volume}}{\text{weight} * 10} * \text{dilution}$$

The ratio A523/A665 is calculated.

Table 2a shows the chlorophyll and anthocyanin absorbance and anthocyanin/chlorophyll-ratio observed on lettuce in Aramon, France (sowing 10 Jan. 2002, transplanting 15 Feb. 2002, harvested 25 Apr. 2002). Line 01P.80146 is an offspring line obtained from plant 99P.38154 by 2 generations of self-fertilisation. Pierrot (Rijk Zwaan), Darkland (Central Valley), Sierra (Vilmorin), and Roxy (Enza) are common lettuce varieties.

Table 2b shows chlorophyll and anthocyanin absorbance and anthocyanin/chlorophyll-ratio observed on lettuce grown in Fijnaart, the Netherlands (sowing 21 May 2002, transplanting 10 Jun. 2002, harvested 20 Aug. 2002). Line 01P.80146 is an offspring line obtained from plant 99P.38154 by 2 generations of self-fertilisation. Pierrot (Rijk Zwaan), Pippo (Rijk Zwaan), Red Rosalita (Johnny's Selected & Orsetti), Darkland (Central Valley), Sierra (Vilmorin), and Roxy (Enza) are common lettuce varieties.

TABLE 2a

| | id. nr. (breeding) | | | | |
|---|---|---|---|---|---|
| | 01P.80146 | Pierrot | Darkland | Sierra | Roxy |
| Total chlorophyll A665 | | | | | |
| Mean | 0.105 | 0.396 | 0.198 | 0.476 | 0.228 |
| Stdev | 0.028 | 0.073 | 0.062 | 0.038 | 0.080 |
| Min | 0.083 | 0.321 | 0.132 | 0.451 | 0.155 |
| Max | 0.150 | 0.486 | 0.279 | 0.520 | 0.353 |
| Nr | 5 | 5 | 4 | 3 | 5 |
| Total anthocyanin A523 | | | | | |
| Mean | 1.589 | 0.883 | 0.006 | 0.033 | 0.087 |
| Stdev | 0.195 | 0.123 | 0.001 | 0.006 | 0.030 |
| Min | 1.370 | 0.725 | 0.005 | 0.029 | 0.063 |
| Max | 1.890 | 1.070 | 0.006 | 0.041 | 0.137 |
| Nr | 5 | 5 | 4 | 3 | 5 |
| Total anthocyanin/ Total chlorophyll: A523/A665 | | | | | |
| Mean | 16.16 | 2.27 | 0.03 | 0.07 | 0.38 |
| Stdev | 4.88 | 0.38 | 0.01 | 0.01 | 0.01 |
| Min | 9.13 | 1.82 | 0.02 | 0.06 | 0.36 |
| Max | 20.17 | 2.68 | 0.04 | 0.08 | 0.40 |
| Nr | 5 | 5 | 4 | 3 | 5 |

TABLE 2b

| | id. nr. (breeding) | | | | | | |
|---|---|---|---|---|---|---|---|
| | Sierra | Roxy | Darkland | 01P.80146 | Red Rosalita | Pippo | Pierrot |
| Total chlorophyll A665 | | | | | | | |
| Mean | 0.570 | 0.267 | 0.343 | 0.063 | 0.278 | 0.456 | 0.325 |
| Stdev | 0.189 | 0.105 | 0.101 | 0.013 | 0.075 | 0.244 | 0.113 |
| Min | 0.345 | 0.180 | 0.205 | 0.049 | 0.205 | 0.244 | 0.196 |
| Max | 0.836 | 0.405 | 0.447 | 0.082 | 0.388 | 0.823 | 0.505 |
| Nr | 5 | 5 | 5 | 5 | 5 | 5 | 5 |
| Total anthocyanin A523 | | | | | | | |
| Mean | 0.038 | 0.046 | 0.010 | 1.228 | 0.030 | 0.693 | 0.870 |
| Stdev | 0.019 | 0.020 | 0.004 | 0.145 | 0.014 | 0.437 | 0.277 |
| Min | 0.028 | 0.027 | 0.005 | 1.042 | 0.017 | 0.371 | 0.474 |
| Max | 0.072 | 0.080 | 0.013 | 1.422 | 0.052 | 1.422 | 1.231 |
| Nr | 5 | 5 | 5 | 5 | 5 | 5 | 5 |
| Total anthocyanin/ Total chlorophyll: A523/A665 | | | | | | | |
| Mean | 0.07 | 0.18 | 0.032 | 20.08 | 0.12 | 1.53 | 2.69 |
| Stdev | 0.02 | 0.05 | 0.01 | 4.09 | 0.08 | 0.46 | 0.31 |
| Min | 0.05 | 0.11 | 0.021 | 15.41 | 0.06 | 1.04 | 2.42 |
| Max | 0.09 | 0.22 | 0.052 | 26.18 | 0.25 | 2.23 | 3.10 |
| Nr | 5 | 5 | 5 | 5 | 5 | 5 | 5 |

Deposit Information

The F5-plants 01R.1439, 02R.2413 and 02R.2418 were deposited on 18 Jul. 2005 with the NCIMB, Ferguson Building, Craibstone Estate, Bucksburn, Aberdeen AB21 9YA, United Kingdom under the deposit accession numbers NCIMB 41337, NCIMB 41338 and NCIMB 41339, respectively.

Various modifications and variations of the described products and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A head-forming lettuce plant of the species *Lactuca sativa* having red leaves throughout the head, including the heart, as in a lettuce plant, representative seeds of which have been deposited with the NCIMB under accession numbers NCIMB 41337, NCIMB 41338 or NCIMB 41339.

2. A head-forming lettuce plant of the species *Lactuca sativa* having red leaves throughout the head, including the heart, obtainable from seed deposited with the NCIMB under accession number NCIMB 41337, NCIMB 41338 or NCIMB 41339.

3. The lettuce plant as claimed in claim 2, wherein the absorbance ratio A523/A665 between anthocyanin and chlorophyll of the heart leaves is between 4 and 50.

4. The lettuce plant as claimed in claim 3, wherein the absorbance ratio A523/A665 between anthocyanin and chlorophyll of the heart leaves is between 9 and 27.

5. The lettuce plant as claimed in claim 2, wherein the absorbance ratio A523/A665 between anthocyanin and chlorophyll of the ten youngest heart leaves larger than 1 cm is between 4 and 50.

6. The lettuce plant as claimed in claim 5, wherein the absorbance ratio A523/A665 between anthocyanin and chlorophyll of the ten youngest heart leaves larger than 1 cm is between 9 and 27.

7. Seed of the lettuce plant as claimed in claim 1 or 2, wherein the seed carries the trait of having red leaves throughout the head, including the heart.

8. A head of the lettuce plants as claimed in claim 1 or 2.

9. A lettuce plant of the species *Lactuca sativa* having red leaves in the heart, obtainable from growing the plant in an environment having an absence of radiation with wavelengths shorter than 400 nm, representative seeds of which having been deposited with the NCIMB under accession number NCIMB 41337, NCIMB 41338 or NCIMB 41339.

10. The lettuce plant as claimed in claim 9, wherein the absence of radiation with wavelengths shorter than 400 nm is in the growing environment during the complete period from sowing until observation.

11. The lettuce plant as claimed in claim 9, wherein the absorbance ratio A523/A665 between anthocyanin and chlorophyll of the heart leaves is between 4 and 50.

12. The lettuce plant as claimed in claim 11, wherein the absorbance ratio A523/A665 between anthocyanin and chlorophyll of the heart leaves is between 9 and 27.

13. The lettuce plant as claimed in claim 9, wherein the absorbance ratio A523/A665 between anthocyanin and chlorophyll of the ten youngest heart leaves larger than 1 cm is between 4 and 50.

14. The lettuce plant as claimed in claim 13, wherein the absorbance ratio A523/A665 between anthocyanin and chlorophyll of the ten youngest heart leaves larger than 1 cm is between 9 and 27.

15. A lettuce plant of the species *Lactuca sativa* having red leaves in the heart from seed as deposited with the NCIMB under accession number NCIMB 41337, NCIMB 41338 or NCIMB 41339.

16. Seed of the lettuce plant as claimed in claim 9 or 15, wherein the seed carries the trait of having red leaves throughout the head, including the heart.

17. A head of the lettuce plant as claimed in claim 9 or 15.

18. A lettuce plant of the species *Lactuca sativa* having red leaves, obtainable from growing the plant during the entire period from sowing until observation in the absence of radiation with wavelengths shorter than 400 nm, representative seeds of which having been deposited with the NCIMB under accession number NCIMB 41337, NCIMB 41338 or NCIMB 41339.

19. The lettuce plant as claimed in claim 18, wherein the absorbance ratio A523/A665 between anthocyanin and chlorophyll is between 4 and 50.

20. The lettuce plant as claimed in claim 18, wherein the absorbance ratio A523/A665 between anthocyanin and chlorophyll is between 9 and 27.

21. The lettuce plant as claimed claim 18, wherein the absorbance ratio A523/A665 between anthocyanin and chlorophyll of the ten youngest heart leaves larger than 1 cm is between 4 and 50.

22. The lettuce plant as claimed in claim 21, wherein the absorbance ratio A523/A665 between anthocyanin and chlorophyll of the ten youngest heart leaves larger than 1 cm is between 9 and 27.

23. Seed of the lettuce plant as claimed in claim 18, wherein the seed carries the trait of having red leaves throughout the head, including the heart.

24. A head of the lettuce plant as claimed in claim 18, wherein the head has red leaves throughout the head, including the heart.

* * * * *